(12) United States Patent
Berbee et al.

(10) Patent No.: US 11,026,569 B2
(45) Date of Patent: Jun. 8, 2021

(54) OTOSCOPE PROVIDING MULTI-DIRECTIONAL ILLUMINATION

(71) Applicant: Wisconsin Alumni Research Foundation, Madison, WI (US)

(72) Inventors: James Berbee, Madison, WI (US); Azita Hamedani, Verona, WI (US); Greg Rebella, Hartland, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/355,061

(22) Filed: Mar. 15, 2019

(65) Prior Publication Data
US 2019/0209001 A1    Jul. 11, 2019

Related U.S. Application Data

(63) Continuation of application No. 14/749,945, filed on Jun. 25, 2015, now abandoned.

(51) Int. Cl.
| | |
|---|---|
| *A61B 1/00* | (2006.01) |
| *A61B 1/05* | (2006.01) |
| *A61B 1/227* | (2006.01) |
| *A61B 1/06* | (2006.01) |
| *A61B 1/07* | (2006.01) |

(52) U.S. Cl.
CPC .......... *A61B 1/227* (2013.01); *A61B 1/00135* (2013.01); *A61B 1/00142* (2013.01); *A61B 1/05* (2013.01); *A61B 1/0615* (2013.01); *A61B 1/07* (2013.01); *A61B 1/00103* (2013.01)

(58) Field of Classification Search
CPC ........................................................ A61B 1/227
USPC .................................................. 600/200, 179
See application file for complete search history.

(56) References Cited

U.S. PATENT DOCUMENTS

| | | | | |
|---|---|---|---|---|
| 4,335,713 | A * | 6/1982 | Komiya | A61B 1/227 600/114 |
| 5,762,605 | A | 6/1998 | Cane et al. | |
| 6,106,457 | A | 8/2000 | Perkins et al. | |
| 6,186,944 | B1 | 2/2001 | Tsai | |
| 6,626,825 | B2 | 9/2003 | Tsai | |
| 7,354,399 | B2 | 4/2008 | Strom et al. | |
| 8,066,634 | B2 | 11/2011 | Andreassen et al. | |
| 2008/0123717 | A1* | 5/2008 | Lane | A61B 1/227 374/209 |
| 2009/0105662 | A1* | 4/2009 | Levedusky | A61B 17/3468 604/192 |
| 2012/0316394 | A1* | 12/2012 | Yoshida | A61B 1/00091 600/123 |
| 2015/0351606 | A1* | 12/2015 | Ruppersberg | A61B 1/00009 600/200 |

* cited by examiner

*Primary Examiner* — Alexandra L Newton
*Assistant Examiner* — Rynae Boler
(74) *Attorney, Agent, or Firm* — Boyle Fredrickson S.C.

(57) ABSTRACT

An otoscope provides a disposable speculum sleeve that conducts light to a narrow tip holding an electronic camera. By removing the light source from the tip, the diameter of the tip may be further reduced to allow the space of the ear canal to be shared between the otoscope and a tool such as a curette for removing foreign objects or to permit the tip to navigate around ear obstructions. The sleeve may provide for multidirectional illumination of the ear structure for improved visualization. The tip and sleeve may be flexible for increased patient comfort when using a compact tip design.

16 Claims, 3 Drawing Sheets

OTOSCOPE PROVIDING MULTI-DIRECTIONAL ILLUMINATION

CROSS REFERENCE TO RELATED APPLICATION

This application is a continuation of U.S. patent application Ser. No. 14/749,945, filed Jun. 25, 2015, hereby incorporated by reference.

BACKGROUND OF THE INVENTION

The present invention relates to an otoscope for inspection of the ear and in particular to an otoscope employing an electronic camera insertable into the ear canal.

An otoscope is a medical device allowing a healthcare professional to inspect the ear canal and tympanic membrane (eardrum). A simple otoscope provides for a hollow funnel-shaped speculum whose small end is inserted into the ear canal. The funnel shape of the speculum stabilizes the otoscope against the ear canal wall and may limit the depth of insertion of the speculum. Modern otoscopes include an internal source of illumination directed down the speculum axis from a contained battery-operated lamp and may provide a magnifying lens supported outside the ear and aligned with the axis of the speculum to provide an enlarged image of the ear structure being viewed.

Recently otoscopes have been developed that include a digital camera fitting within the speculum to permit the documentation of a diagnosis by image capture. U.S. patent application Ser. No. 14/461,103 filed Aug. 15, 2014, assigned to the assignee of the present invention and hereby incorporated by reference, discloses an otoscope having the camera mounted on a distal end of a flexible stalk of narrow diameter. The small size of the stalk permits improved access to the ear canal possibly in conjunction with other instruments. The flexibility of the stalk moderates the pressure that may be applied to the ear canal by contact with the small diameter of the stalk. Light emitting diodes surround the camera at the end of the speculum to direct axial light toward the field of view of the camera.

SUMMARY OF THE INVENTION

The present invention provides an otoscope employing a light pipe in the speculum, surrounding a stalk that holds a camera, to deliver light to the inner ear. The light pipe moves the light source away from the tip of the speculum permitting an even narrower outside diameter of the speculum. In addition, the light pipe may have an exposed diffuser surface before its tip to disperse the light into the ear canal and ear tissue providing multidirectional illumination for improved viewing of ear structure.

Specifically, in one embodiment, the invention provides an otoscope having a housing that may be held and supported adjacent to an outer ear of a patient and which includes an elongate probe element having a proximal end supported by the housing so that a distal end of the elongate probe element may extend along an axis into the ear canal of the outer ear in the inspection position. An electronic camera is supported at the distal end of the elongate probe element for viewing into the ear canal when the distal end of the elongate probe element is in the inspection position in the ear canal. A coaxial sheath, positioned around the probe element, conducts light from a proximal end of the sheath to a distal end of the sheath proximate to the electronic camera.

It is thus a feature of at least one embodiment of the invention to provide an improved light delivery system for an otoscope that can reduce the probe size and provide improved illumination.

The coaxial sheath may be a tubular light pipe.

It is thus a feature of at least one embodiment of the invention to provide a light that is easily fabricated, for example, in the shape of the speculum.

The outer diameter of the coaxial sheath at a distal 0.5 or one centimeter length of the coaxial sheath may be less than 5 millimeters or less than three millimeters.

It is thus a feature of at least one embodiment of the invention to provide an extremely narrow otoscope probe that is easier to maneuver (for example, around obstructions) and which can share the ear canal with other instruments.

The coaxial sheath, when surrounding the elongate probe, may be coated with an elastomer to reduce pressure against the patient's ear canal.

It is thus a feature of at least one embodiment of the invention to provide a small diameter otoscope probe that is nevertheless comfortable to the patient with the flexing reducing contact force between the otoscope probe and ear canal.

The coaxial sheath may be constructed at least in part of a transparent elastomeric material.

It is thus a feature of at least one embodiment of the invention to impart flexibility by using a resilient material.

A distal portion of the coaxial sheath, before the distal end of the coaxial sheath, may emit light in a direction having a lateral component perpendicular to the axis. For example, the distal portion may be a substantially light conducting tube emitting light radially with respect to the tube axis.

It is thus a feature of at least one embodiment of the invention to provide a more diffuse illumination of ear structure such as reduces brightness variation and hotspot reflection.

The distal portion may include a light diffusing outer surface.

It is thus a feature of at least one embodiment of the invention to provide moldable feature that couples conductive light and disperses it at multiple radial angles for multidirectional illumination.

The distal portion may provide an outer surface presenting radially extending ridges or bristles for removal of material from the ear canal.

It is thus a feature of at least one embodiment of the invention to incorporate tool surfaces into the otoscope in proximity to the end of the probe.

The coaxial sheath may include mechanical retention elements cooperating with corresponding elements on the housing for releasably attaching the coaxial sheath to the housing through an applied force to the coaxial sheath.

It is thus a feature of at least one embodiment of the invention to provide a light pipe that can do double duty as a disposable speculum.

The applied force may be a torsional force about the axis.

It is thus a feature of at least one embodiment of the invention to provide an attachment method familiar to users of conventional otoscope speculums.

The elongate probe may be supported on the housing by a retraction mechanism allowing extension and retraction of the elongate probe along the axis with respect to the housing.

It is thus a feature of at least one embodiment of the invention to permit retraction of the probe to protect the probe when the speculum is removed.

The sheath may cooperate with the retraction mechanism to retract the elongate probe when the sheath is removed from around the elongate probe and to extend the elongate probe when the sheath is installed around the elongate probe.

It is thus a feature of at least one embodiment of the invention to provide automatic retraction of the probe when the protective sheath is removed and extension of the probe when the protective sheath is installed reducing the chance of damage to the camera.

The cooperation between the sheath and the retraction mechanism may include a helical internal thread on the sheath.

It is thus a feature of at least one embodiment of the invention to permit a familiar attachment method for the sheath to trigger the extension and retraction of the probe.

The sheath may include an optically transparent portion covering the camera so that the camera field of view extends through the optically transparent portion.

It is thus a feature of at least one embodiment of the invention to make use of the transparent light conducting material of the sheath to provide a protective and sterile field-preserving window over the camera lens.

The housing may include a detachable grip portion extending in a direction having a component perpendicular to the axis for supporting the otoscope with a single hand gripping the grip portion.

It is thus a feature of at least one embodiment of the invention to permit the otoscope to work with standard otoscope charging stations and stands and the associated grips received by those charging stations and stands.

The otoscope may further include a barcode decoder for receiving signals from the camera imaging a barcode to decode the barcode.

It is thus a feature of at least one embodiment of the invention to permit the otoscope to capture barcodes that may be used to link acquired images to patient files.

These particular objects and advantages may apply to only some embodiments falling within the claims and thus do not define the scope of the invention.

DETAILED DESCRIPTION OF THE PREFERRED EMBODIMENT

Figure 1:
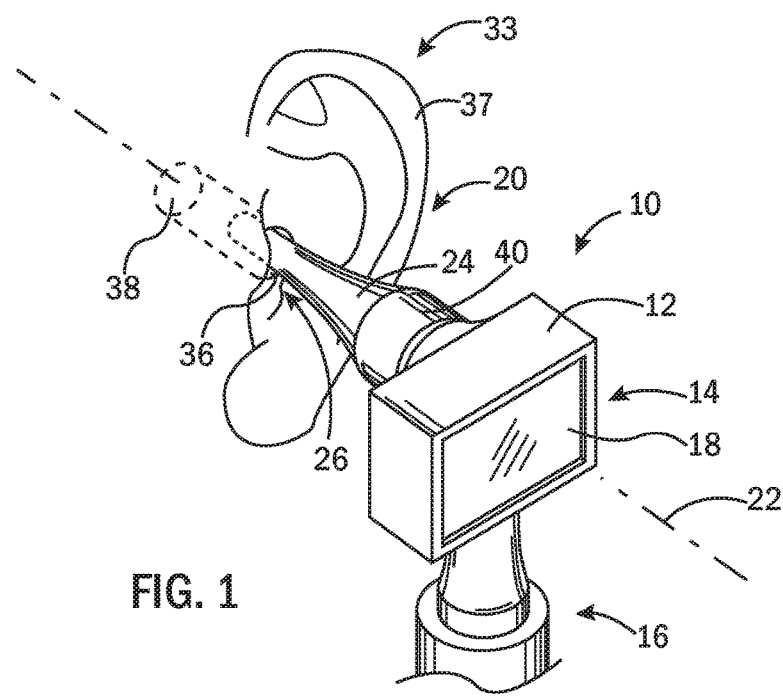
FIG. 1 is a perspective view of an otoscope constructed according to the present invention providing a housing presenting on a front side an electronic display and on a rear side having a camera on a probe element extending away from the electronic display for insertion into the ear canal and covered by a disposable speculum.

Referring now to FIG. 1, an otoscope 10 of the present invention may provide a housing 12 having a head portion 14 and a detachable grip portion 16. The grip portion 16 is sized to be grasped by the hand of a healthcare professional in the manner of a conventional otoscope with the grip portion 16 extending generally upward from the healthcare professional's hand to the head portion 14.

A front surface of the head portion 14 may provide for an electronic display 18, for example, being a backlit three-color liquid crystal display (LCD) of a type known in the art. An elongate probe assembly 20 may extend from a rear face of the head portion 14 in a direction away from the display 18 along an axis 22 normal to the surface of the display 18. The probe assembly 20 may include a generally conical sheath 24 constructed at least in part of the transparent thermoplastic material to provide for light conducting properties as will be described below.

As is generally understood, the outer ear 33 of a human patient includes the pinna 37 providing a sound collecting structure. The pinna 37 surrounds an ear canal 36 leading to and terminating at the tympanic membrane or eardrum 38. A length of the ear canal 36 in an average adult human is approximately 2.5 centimeters and the ear canal 36 has an average diameter of approximately 0.7 centimeters.

Figure 2:
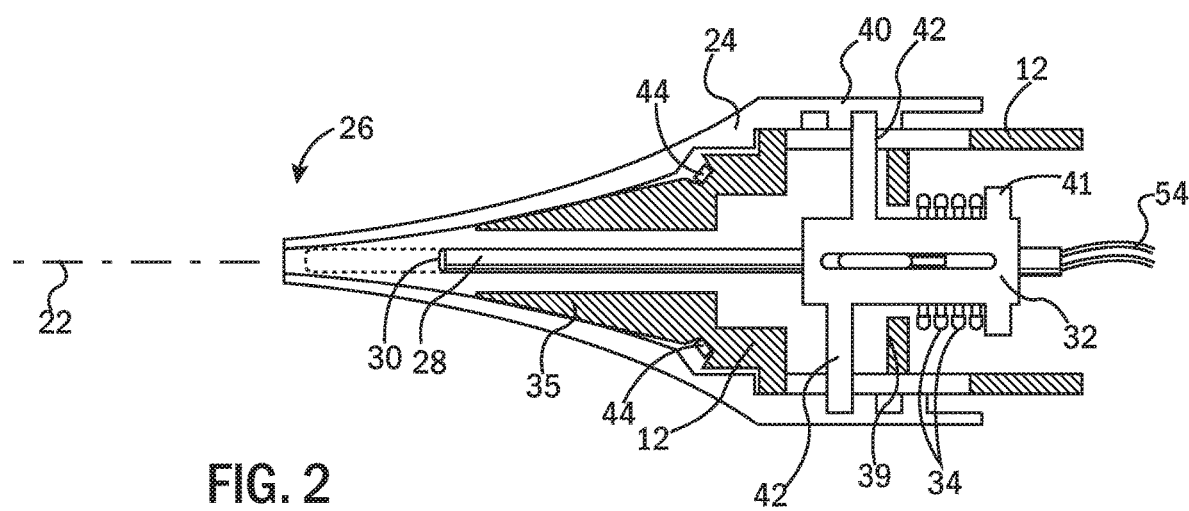
FIG. 2 is an elevational cross-section through the probe element and the disposable speculum showing a mechanism for retracting the probe element and camera when the speculum is removed and extending the probe element and camera when the speculum is in place.

Referring now also to FIG. 2, the sheath 24 may taper inward as one moves away from the head portion 14 to a distally located sheath tip 26. The sheath 24 provides a central bore which holds an extendable cylindrical probe 28 having on its distal tip a front facing electronic camera 30 for acquiring multi-pixel, three-color images in a field of view directed along the axis 22. Electronic camera 30 may, for example, be a self-contained charge coupled device (CCD) camera such as is commercially available providing, for example, a measurement area of 1.4 mm diagonal and 62,500 pixels.

A proximal end of the cylindrical probe 28 is supported by a spring-loaded slider 32 that may move along the axis 22 with respect to structure of the housing 12 generally constrained for translational motion only. A helical compression spring 34 may extend between an inwardly extending flange 39 of the housing 12 and a rearward radially outwardly extending flange 41 on the slider 32 to bias the slider 32 in a retraction direction withdrawing the camera 30 within a protective sleeve 35. The sleeve 35 is fixed with respect to the housing 12 and surrounds the camera 30 for protection when the camera 30 is fully retracted.

A proximal end of the conical sheath 24 may provide for a collar 40 having internal threads that can engage outwardly extending pins 42 of the slider 32. Clockwise rotation of the collar 40 (looking toward the proximal end) pulls the pins 42 forward toward the sheath tip 26 of the sheath 24 while pulling the sheath 24 onto the housing 12. Forward motion of the pins 42 moves the slider 32 forward against the force of the spring 34 extending the camera 30 to a position proximate to the sheath tip 26. Thus, the fragile camera 30 is exposed only when the protective sheath 24 is in place. A detent feature on the housing 12 (not shown) may lock the collar 40 against dislodgment or, alternatively, friction provided by the force between the internal threads and the pins 42 may serve the same purpose.

Figure 3:
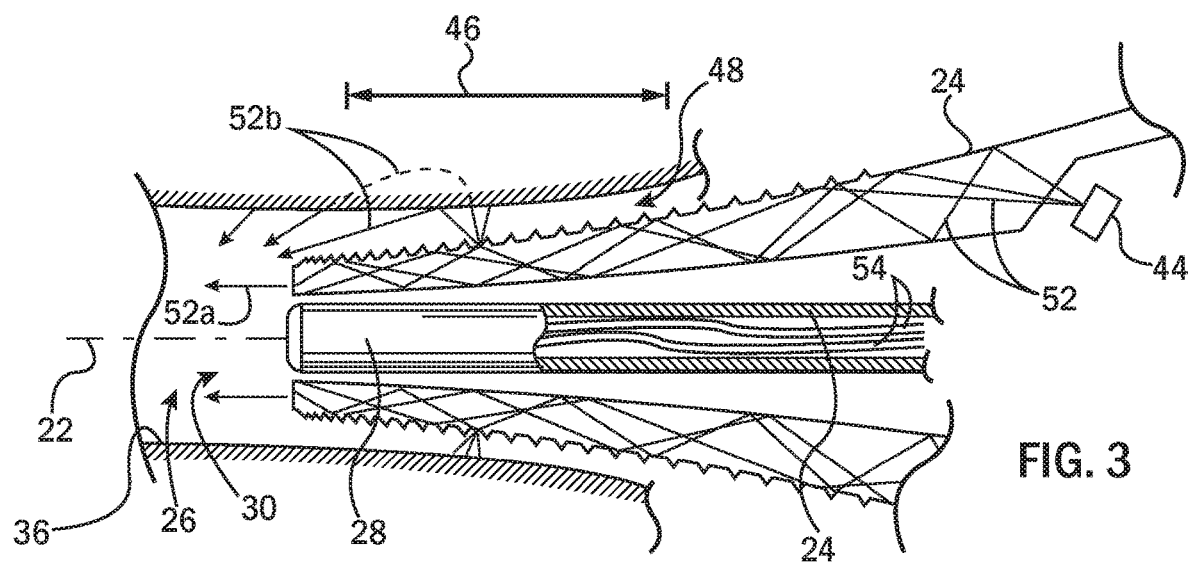
FIG. 3 is a detailed fragmentary view of FIG. 2 with the camera element fully extended showing radial and axial illumination of the ear canal such as creates a diffuse lighting for better resolving ear structure.

Referring now also to FIG. 3, all or part of the sheath 24 may be constructed of a transparent material so that light emitting diodes 44 mounted on the structure of the housing 12 may project light 52 into a proximal portion of the conical sheath 24. From there, the light 52 may be conducted by internal reflection in the manner of a light pipe to the distal sheath tip 26 of the conical sheath 24. The light emitting diodes 44, as attached to structure of the housing 12, will be retained when the conical sheath 24 is removed and may be oriented to face a feature on the conical sheath 24 that promotes coupling of light 52 from the LEDs 44 into the conical sheath 24, for example, an optical flat perpendicular to the direction of light propagation.

In one embodiment, the LEDs 44 may provide for a combination of red, green, and blue elements so that the hue of the project light 52 from the LED 44 may be controlled, for example, to accentuate certain ear structure. At the sheath tip 26 a portion of light 52a exits in a direction parallel to the axis 22; however, some light 52b in a distal region 46 of the sheath 24, before sheath tip 26, may be coupled by a diffusing roughness 48 on the outer surface of the sheath 24 out of the sheath 24 to provide light 52b emanating along a radial direction from the sheath 24 to strike the walls of the ear canal 36. This light 52b, through reflection and scattering between the outer surface of the sheath 24 and the walls of the ear canal 36 and through internal conductance to the tissue of the ear canal 36, provides diffuse multi-angle illumination of the ear structure in the ear canal providing improved viewing of that structure through more uniform illumination and illumination arriving at multiple angles. The region 46 may be, in one embodiment, five millimeters in length along the axis 22 and as much as one and a half centimeters in some embodiments.

Figure 4:
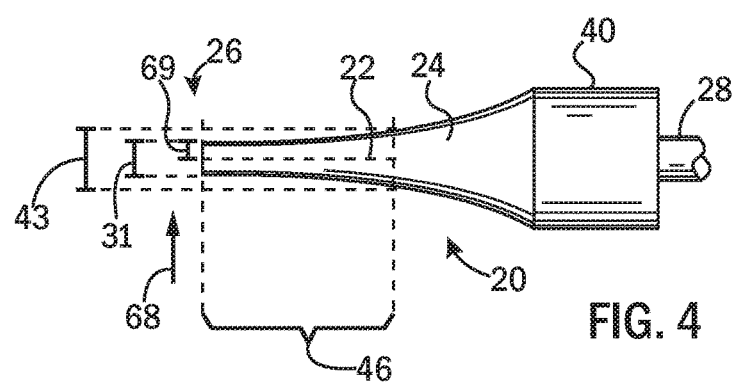
FIG. 4 is a side elevational view of the speculum installed on the probe element showing flexibility of the combined assembly.

Referring now to FIG. 4, the diameter 31 of the sheath tip 26, measured in a plane perpendicular to the axis 22, may be less than two millimeters and the diameter 41 of the sheath 24 in the distal region 46, extending from the sheath tip 26 along the axis 22 by at least five millimeters and in one embodiment one centimeter, may be less than five millimeters and in some embodiments less than three millimeters to be substantially smaller than the ear canal 36. It is intended that the sheath 24 that surrounds the camera 30 be sized to allow imaging of the eardrum 38 past minor obstructions, such as normally present earwax, and to allow passage within the ear canal 36 by medical instruments such as a curette for removing obstructing bodies such as earwax while probe assembly 20 is in place for imaging, that is, to permit instruments to extend to the side and pass the end of the sheath tip 26.

Referring still to FIG. 4, as noted above, the present invention provides a sheath tip 26 that is more flexible than a typical otoscope speculum. Generally the flexibility of the sheath tip 26 is intended to improve the comfort to the patient and reduce risk of damage to structure of the outer ear 33 caused by a small diameter probe. When the head portion 14 is stabilized, a perpendicular force 68 applied to the distal end of the sheath tip 26 of 100 grams will cause a deflection 69 of no less than one millimeter. In contrast, a similar force applied to the end of the atypical speculum will provide a corresponding deflection at the end of the speculum of much less than one millimeter. It will be appreciated that this flexibility may be provided by constructing the cylindrical probe 28 and conical sheath 24 from a flexible material or by mounting the cylindrical probe 28 and conical sheath 24 to the housing 12 through a flexible or compliant mount that allows a tipping of these elements in response to applied lateral force, or by a coating of the cylindrical conical sheath by elastomeric material, or by a combination of these approaches.

Figure 5:
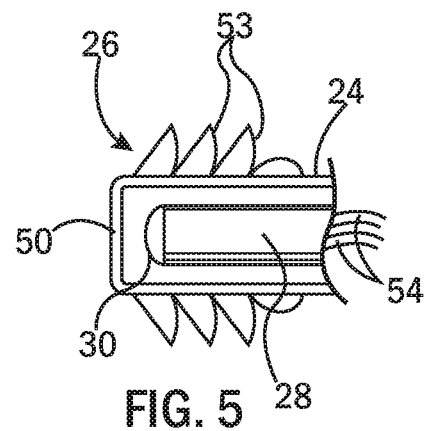
FIG. 5 is a detailed cross-section of the distal end of FIG. 4 showing radial teeth on the speculum for assisting in the removal of foreign material from the ear canal and showing a lens protector incorporated into the disposable speculum.

Referring now to FIG. 5, the sheath tip 26 of the sheath 24 may be closed by an optically transparent, low distortion window 50 allowing images to be detected therethrough while protecting the camera 30 from contamination while also providing a sterile shield between the camera 30 and patient. An outer surface of the sheath 24 proximate to the sheath tip 26 may include rearwardly canted bristles or teeth 53 that may serve the purpose of assisting in the removal of debris and material from the ear canal 36 using the sheath 24 itself. These teeth 53 may be formed simultaneously with the material of the sheath 24 to be optically clear and therefore to pass illumination. Alternatively, the teeth 53 may be overmolded of a flexible elastomeric material such as silicone rubber thereby serving also to reduce the pressure between the sheath tip 26 and the ear canal 36 by a cushioning operation.

The cylindrical probe 28 may be constructed of a relatively flexible material such as a silicone or polyvinyl chloride material and may be tubular to provide a passage for electrical conductors 54 communicating pixel image data from the camera 30.

Figure 6:
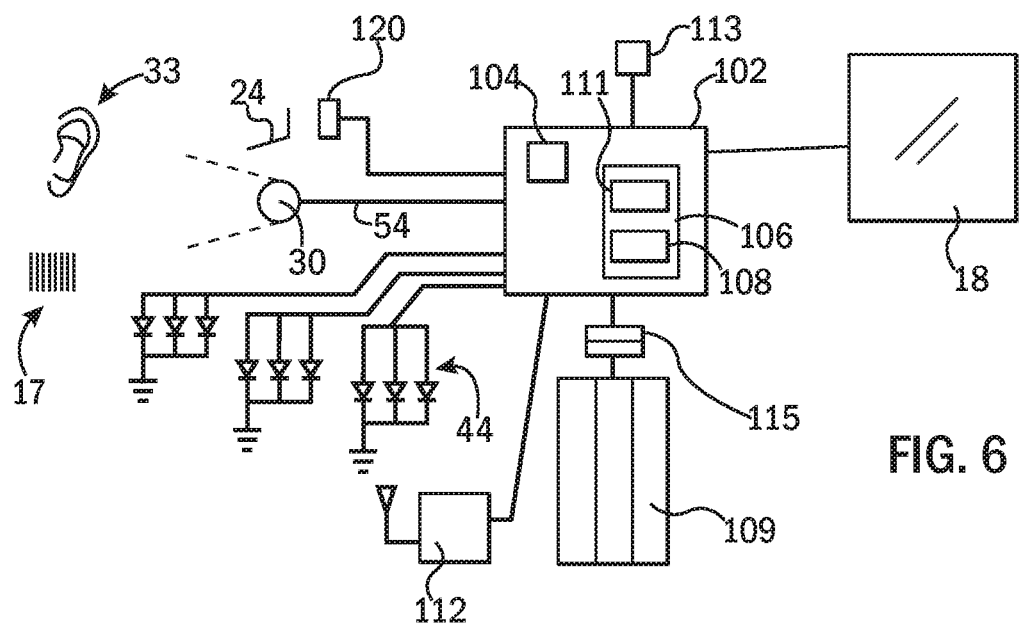
FIG. 6 is a simplified block diagram of the electronics of the otoscope of FIG. 1.

Referring now to FIG. 6, the otoscope 10 may incorporate an electronic controller 102 such as a microcontroller being in essence an electronic computer and I/O circuitry. The controller 102 will provide a processor 104 communicating with a memory 106 permitting non-transient storage of a program 108. Generally the program 108 will provide for the receipt of signals from the camera 27 and the display on display 18 of images from the camera and will provide for transmission of such images to affiliated equipment, for example, a PACS device. Program 108 may perform normal image processing, for example, exposure control, contrast adjustment, color balance and the like. The program 108 through the controller 102 may also control the illumination of the LEDs 66 as part of the exposure control process. In addition the memory 106 may hold a barcode decoder program 111 allowing the otoscope 10 to also be used for reading data from barcodes 117, for example, to identify a particular image to a particular patient's file and transmit that barcode data with images in a protocol for linking the two.

The controller 102 may also communicate either through a wireless transceiver 112 or an electrical connector 114 with other devices, for example, to permit the transmission of image data and barcode data to a remote electronic medical record server.

A power button 113 may communicate with the controller 102 to put electronic circuitry into a low power sleep state, disabling the display 18, camera 27, and LEDs 66.

The program 108 in a standby mode may cycle through different colors on the LEDs 44 or display particular colors (e.g., pink) to improve the attractiveness of the otoscope 10 for pediatric patients who may be fearful of medical equipment. The otoscope circuitry described above may be powered by a battery 109 contained in a grip that may be removably connected to the housing 12 by electrical and mechanical connector 115.

A sleeve detector switch 120 may also be provided to detect whether sheath 24 is in place before activating the otoscope 10 to prevent use of the otoscope 10 without a protective sheath 24.

It will be appreciated that the sheaths 24 are constructed to be relatively low-cost and therefore disposable, for example, such as may be manufactured by injection molding, and in this regard a variety of different sleeve types may be provided, for example, having different teeth designs for different purposes including other medical inspection of the nose or the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

"Diameter" as used herein should not be understood to require a cylindrical or circular element but to simply describe a diameter of a circumscribing cylinder closely conforming to the element.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

What we claim is:

1. An otoscope comprising:
   a housing adapted for support by a hand of a healthcare professional and having a housing distal end;
   an elongate probe element having a probe proximal end movably attached to the housing so that a probe distal end of the elongate probe may extend between an extension position beyond the housing distal end and a retraction position retracted from the extension position;
   an electronic camera supported by the probe distal end for viewing into the ear canal; and
   a sheath having a sheath proximal end removably coupled to the housing and extending beyond the housing distal end to cover at least a portion of the elongate probe beyond the housing distal end when the elongate probe is in the extension position.

2. The otoscope of claim 1 wherein the housing provides a sleeve along the axis within which the elongate probe may slide when moving between the extension and retraction position so that the elongate probe is protected within the sleeve in the retraction position.

3. The otoscope of claim 2 wherein the sleeve surrounds the elongate probe and flares outward toward the housing to a diameter greater than that of an ear canal.

4. The otoscope of claim 2 wherein the sheath provides inelastic sidewalls tapering inward from the housing to a sheath tip sized to fit within the ear canal and having a central bore sized to receive the elongate probe therein.

5. The otoscope of claim 4 wherein the sheath includes retention elements cooperating with corresponding elements on the housing for releasably attaching the sheath to the housing over the sleeve.

6. The otoscope of claim 5 wherein the retention elements between the sheath and the retraction mechanism includes a helical internal thread on one of the sheath and housing.

7. The otoscope of claim 4 wherein the sheath cooperates with a retractor attached to the housing and providing a support end movable between an extension and retraction position to retract the elongate probe when the sheath is removed from the housing and to extend the elongate probe when the sheath is attached to the housing.

8. The otoscope of claim 7 wherein the retractor is a spring loaded slider moving the elongate probe element along the axis between a retraction position and an extension position and biasing the elongate probe in the retraction direction.

9. The otoscope of claim 8 wherein the electronic camera is surrounded by the sheath proximate the sheath tip when the elongate probe element is in the extension position.

10. The otoscope of claim 4 wherein an outer diameter of the sheath at a distal 0.5 centimeter length of the sheath is less than 5 millimeters.

11. The otoscope of claim 4 wherein the outer diameter of the sheath at a distal 1 centimeter length of the sheath is less than 3 millimeters.

12. The otoscope of claim 4 wherein the sheath tip provides an outer surface presenting radially extending ridges or bristles for removal of material from the ear canal.

13. The otoscope of claim 4 wherein the sheath flexes no less than 1 mm when 100 g force is applied to the sheath tip.

14. The otoscope of claim 1 wherein the elongate probe element is a tube providing passage of electrical conductors to the electronic camera.

15. The otoscope of claim 1 wherein the elongate probe element is constructed of at least one of a silicone and a polyvinyl chloride.

16. The otoscope of claim 1 wherein the housing includes a detachable grip portion extending in a direction having a component perpendicular to the axis for supporting the otoscope with a single hand gripping the grip portion.

* * * * *